(12) United States Patent
Takahashi

(10) Patent No.: US 6,563,902 B2
(45) Date of Patent: May 13, 2003

(54) ENERGY DISPERSIVE X-RAY ANALYZER

(75) Inventor: Haruo Takahashi, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/893,715

(22) Filed: Jun. 28, 2001

(65) Prior Publication Data

US 2002/0009177 A1 Jan. 24, 2002

(30) Foreign Application Priority Data

Jul. 5, 2000 (JP) .......................................... 2000-204073

(51) Int. Cl.$^7$ ............................................. G01N 23/223
(52) U.S. Cl. ......................................... 378/49; 378/115
(58) Field of Search .............................. 378/44, 45, 49, 378/114, 115, 116

(56) References Cited

U.S. PATENT DOCUMENTS 4,121,098 A * 10/1978 Jagoutz et al. ................ 378/49
2002/0071519 A1 * 6/2002 Satoh ........................... 378/49

* cited by examiner

Primary Examiner—Robert H. Kim
Assistant Examiner—Hoon K. Song
(74) Attorney, Agent, or Firm—Adams & Wilks

(57) ABSTRACT

In order provide an energy dispersive X-ray analyzer that can perform efficient measurement by optimizing signal processing time of an X-ray counting section, an energy dispersive X-ray analyzer is provided with an energy dispersive X-ray detector, an X-ray counting section for analyzing the signal from the energy dispersive X-ray detector and generating a frequency distribution for each energy level, namely an energy spectrum, and a data control section for performing data processing, user interface etc. The X-ray counting section of the energy dispersive X-ray analyzer has signal processing methods with different processing times for a single X-ray input, and a function for selecting which method result to make use of using input X-ray energy.

2 Claims, 3 Drawing Sheets

ENERGY DISPERSIVE X-RAY ANALYZER

BACKGROUND OF THE INVENTION

The present invention relates to X-ray counting circuit technology for an energy dispersive X-ray analyzer.

In an X-ray counting section of an energy dispersive X-ray analyzer, a counting efficiency representing a ratio of incoming X-rays to X-rays actually counted, and an energy resolution for the acquired energy spectrum are mutually conflicting elements. There are differences in absolute values due to performance of respective devices, but there is a relationship such that if the energy resolution is made good the counting efficiency becomes poor, while if the counting efficiency is made good the energy resolution becomes poor. The reasons for this are as described in the following. In order to obtain a satisfactory resolution, more information is required. What this means in actual fact is that the processing time per X-ray input is required to be longer. In the event that the next X-ray is input within the processing time, the information of the X-ray input before is disrupted by the X-ray information input later, which means that those two signals become discarded. Since X-ray input is a random phenomenon, making the processing time longer in order to improve resolution will increase the probability of subsequent X-rays being injected during processing causing discard of data, and counting efficiency will become worse. As a result, a processing time having a suitable balance between energy resolution and counting efficiency is selected depending on the use.

In a conventional energy dispersive X-ray analyzer, this processing time, namely a balance between energy resolution and counting efficiency, is generally the same across detectable energy regions.

Accordingly, in actual application, there are many instances where the same energy resolution is not required for all regions. In these type of cases, unnecessary signals that conventionally require a long processing time, such as those for energy regions that are not of interest for application or energy regions that have no application problems for the reason of being separated from the energy of characteristic X-rays, also contribute to worsening of the counting efficiency, and there is a problem that an unnecessarily long time is expended on measurement. With the present invention, attention is paid to this point, and the purpose is to provide an energy dispersive X-ray analyzer that can perform efficient measurement, by optimizing signal processing time of an X-ray counting section.

SUMMARY OF THE INVENTION

In order to achieve the above stated purpose, an energy dispersive X-ray analyzer of the present invention is provided with an energy dispersive X-ray detector for detecting X-rays and outputting a signal containing energy information of detected X-rays, an X-ray counting section for analyzing the signal from the energy dispersive X-ray detector and generating a frequency distribution for each energy, namely an energy spectrum, and a data control section for performing data processing, and user interface etc. The X-ray counting section of the energy dispersive X-ray analyzer has signal processing methods with different processing times per X-ray input, and a function for selecting which method to make use of using input X-ray energy.

DETAILED DESCRIPTION OF THE PREFERRED EMBODIMENT

Figure 1:
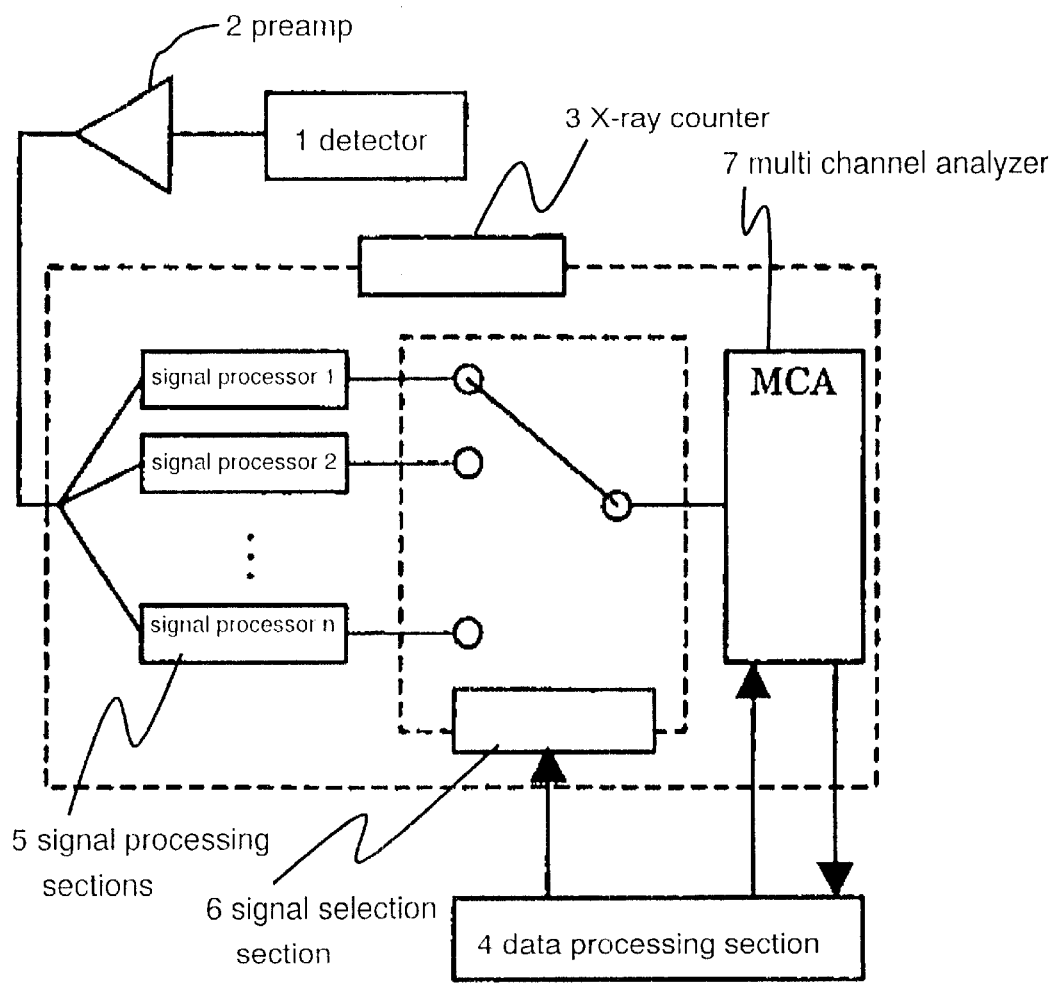
FIG. 1 is a block diagram schematically showing of an energy dispersive X-ray analyzer of the present invention.

One example of an energy dispersive X-ray analyzer of the present invention will be described in detail in the following based on the drawings. First of all, an outline of the overall operation of the energy dispersive X-ray analyzer will be given based on FIG. 1, and then detailed embodiments of the X-ray counting section will be described based on FIG. 2 and FIG. 3.

If X-rays are incident into a semiconductor detector 1, a current pulse having a total amount of electric charge proportionate to the incident X-ray energy is generated. A detection section contains a preamp 2 for converting the generated current pulse to a voltage pulse, and the voltage pulse is input to the X-ray counting section. At the X-ray counting section, for a single input, a plurality of signal processing sections 5 are operating simultaneously. However, these sections have respectively different processing times, and a favorable energy resolution is obtained with systems having quite long processing times, but the probability of adjacent pulses overlapping in time is high. The output from these signal processing systems is sent to a signal selecting section 6, which selects which signal processing system value is to be used based on an output value of a signal processing system having the shortest processing time, that is, the system acquiring results in the quickest time. Data constituting a reference for determination, namely data indicating correspondence between energy and the signal processing sections, can be set form a data processing section 4. Also, with an energy dispersive X-ray analyzer having restricted application, it is possible to have an embodiment having a fixed judgment reference in the X-ray counting section without going through the data processing section.

By performing selection in this way, data of a particular signal processor is sent to a multi channel analyzer 7. By repeating this process, an energy spectrum of X-rays incident to the detector is acquired, and the data processing section 4 performs processing according to the purpose of use. The operation of an energy dispersive X-ray analyzer of the present invention has been outlined above.

Figure 2:
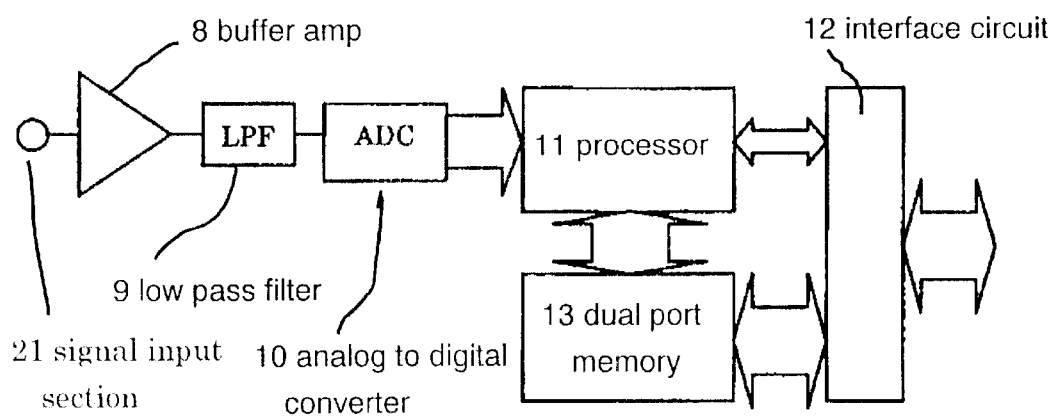
FIG. 2 is a drawing showing an embodiment of an X-ray counting section of an energy dispersive X-ray analyzer of the present invention.

Next, an X-ray counting section of the energy dispersive X-ray analyzer of the present invention, capable of selecting a signal processing method according to X-ray energy, will be described in detail. One example of an X-ray counting section contained in the energy dispersive X-ray analyzer of the present invention is shown in FIG. 2. In this example, the point that can be handled by a plurality of signal processing systems without causing degradation in signal quality, and a system using digital signal processing taking into consideration the ease of realizing functions to diverge processing according to the energy size will be described, but it is also possible to realize by applying a plurality of analog waveform shaping circuits and control circuits, which can be considered modifications to the present invention.

A signal from the detection section that has been input from the signal input section 21 is received by a buffer amp 8, and after unnecessary frequency components have been removed by a low pass filter 9 it is sampled using an analog to digital converter 10 and the input signal is subsequently handled as a digital sequence. The sampled sequence described above is taken into a processor 11, detection of incoming X-rays and selection of an energy analysis method are carried out inside the processor, and finally the energy is obtained. The rank to which x-ray energy output from the processor belongs is represented as an address in a dual port memory 13, and an energy spectrum is constructed by registering the number of X-rays incident at this address. An interface circuit 12 is used for exchanging data stored in the dual port memory 13 and exchanging setting information corresponding to energy regions and the signal processing method.

Figure 3:
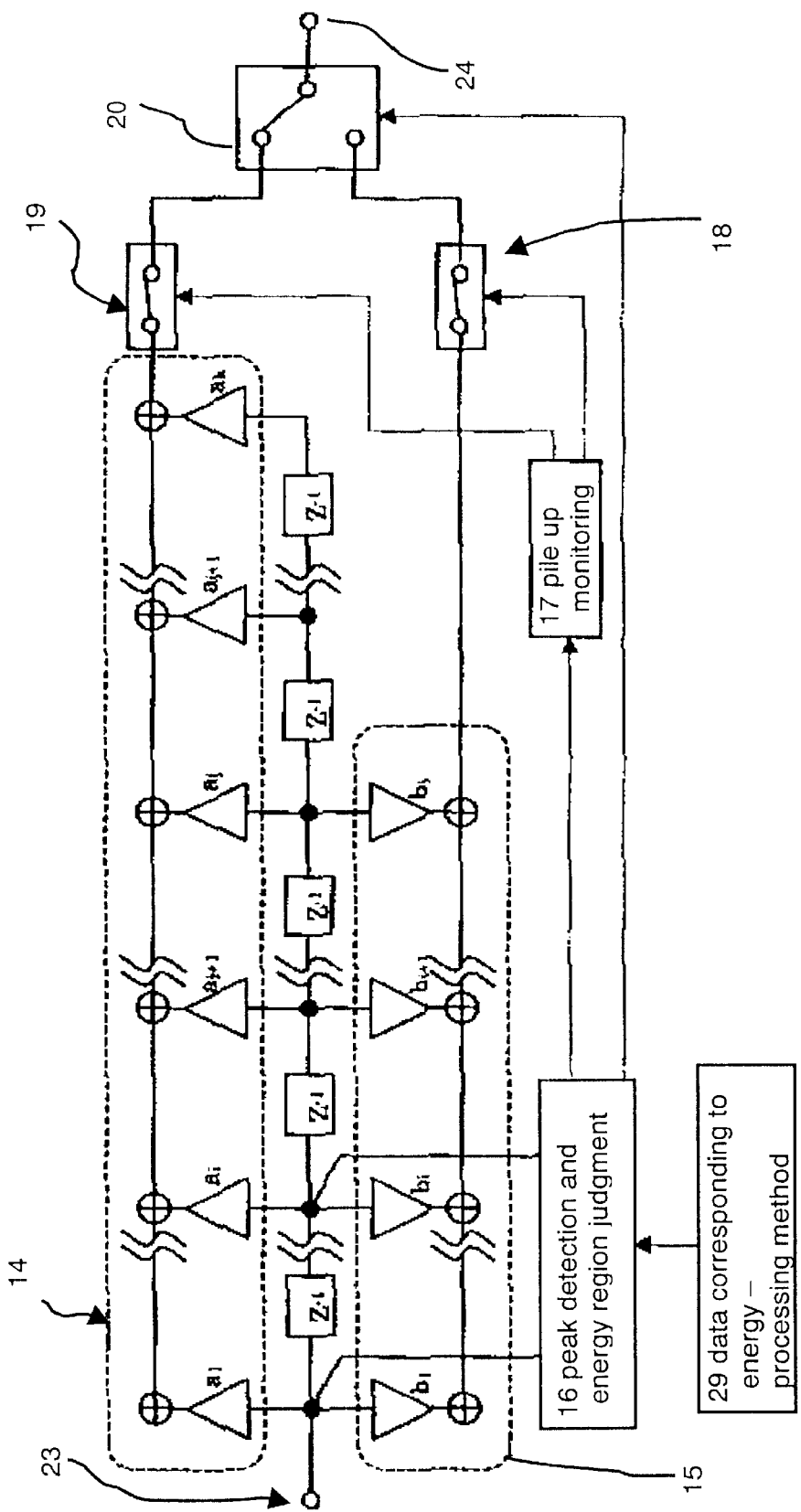
FIG. 3 is a drawing showing the concept of processing inside a processor (11) of the embodiment shown in FIG. 2.

One embodiment of processing inside the processor is shown schematically in FIG. 3. If data sampled by the analog to digital converter 10 is taken in from the signal capture section 23, it is processed by a two system digital filter made up of a high resolution processing system 14 and a high speed processing system 15. The input signal is simultaneously sent to the block 16 for peak detection and energy region judgment. In this block, peaks are detected by looking at patterns of input signal change, and at the same time energy is judged by carrying out digital filter processing in response to a filter length from 2–4. The judged energy is compared to data 29 corresponding to energy regions and a processing method and a selection is made as to whether the output from the high resolution system 14 or the output of the high speed system 15 is used. The judged result is notified to a pile up monitoring block 17. In the pile up monitoring block 17, it is monitored whether or not peaks are detected in time intervals appropriate to filter length of respective signal processing systems before and after the signal that has been peak detected. If the next peak is detected inside the time interval, data is invalidated by overlapping that peak with the peak before. When the next peak is not detected within the processing time of the selected signal processing system, the block 16 for peak detection add energy region judgment sends an output value to the interface section 24 with the dual port memory at a timing corresponding to the selected signal processing, and stores spectrum data.

In the embodiment described here, there are two signal processing systems, but it is also possible to have a plurality of processing systems, as required.

Also, with the previously described embodiment, it has been described that a signal processing method is uniquely decided for energy, but a variation is possible such that a signal processing method for obtaining good energy resolution is selected in a particular energy region, and in other energy regions, a signal processing method for obtaining good energy resolution is used when there is no pile up, and a signal processing method with low energy resolution, namely a short processing time, is only used when it is possible to avoid overlapping with the previous peak by using a signal processing method with low energy resolution.

Figure 4A:
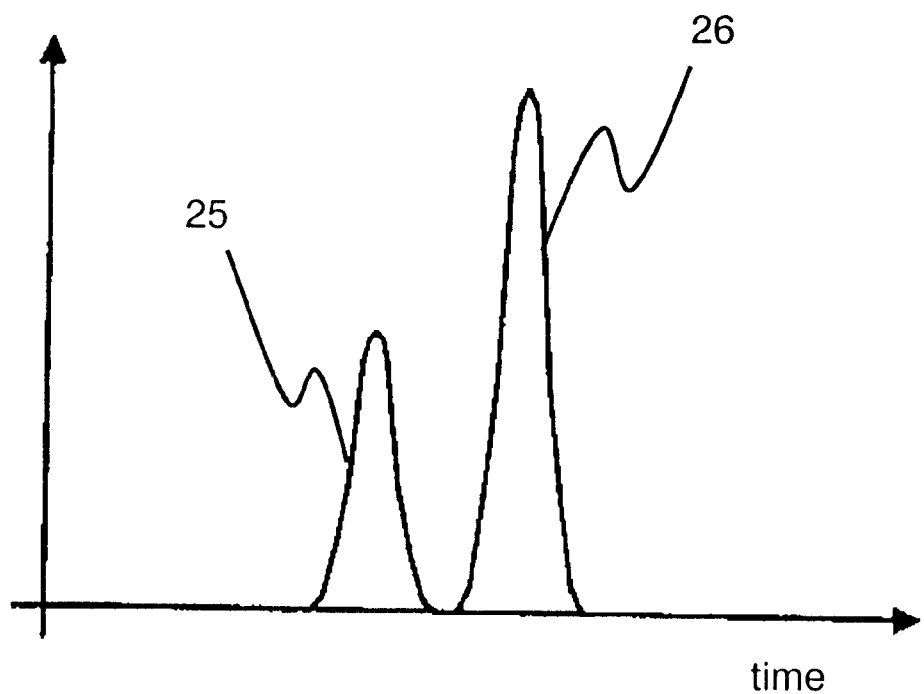
FIG. 4A shows the appearance when performing two different signal processing schemes for the same input.
Figure 4B:
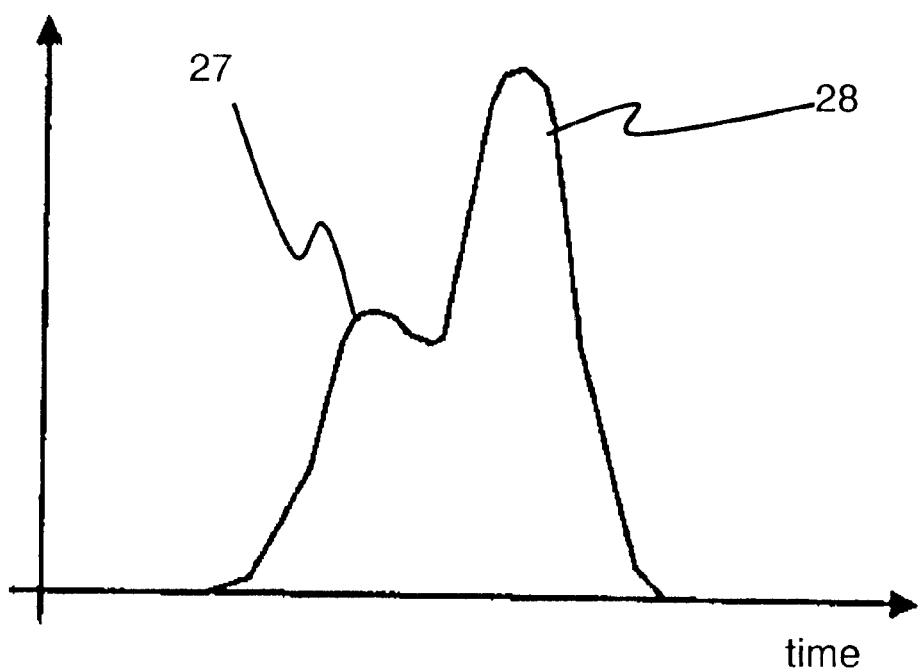
FIG. 4B shows the appearance when performing two different signal processing schemes for the same input, and represents processing that has a long processing time per single pulse, but is excellent with respect to energy resolution of acquired results.

In order to explain the present invention, a simple example will be given, as shown in FIGS. 4A and 4B. FIGS. 4A and 4B shows the appearance when performing two different signal processing schemes for the same input. FIG. 4B represents processing that compared to FIG. 4A has a long processing time per single pulse, but is excellent with respect to energy resolution of acquired results. In both FIG. 4A and FIG. 4B, the horizontal axis represents time, and the vertical axis represents signal processing output. In this graph, one peak represents input of a single X-ray, and the peak height represents the size of the energy of the input X-ray. That is, in the range represented in this drawing, X-rays are input twice, with the energy of the first peaks 25 and 27 being higher than that of the second peaks 26 and 28. For example, energy regions corresponding to the high peaks 26 and 28 are considered not to require such high resolution. With the method of the related art, for regions requiring the best energy resolution, a processing method like FIG. 4B is selected, peaks 27 and 28 not requiring very good energy resolution as results are overlapped, and valid data is not acquired. If the energy dispersive X-ray analyzer of the present invention is used, the two signal processing schemes of FIG. 4A and FIG. 4B are carried out, and for X-rays having higher energy input later, it is possible to select a signal processing method of FIG. 4A, and it is possible to produce valid data.

With an X-ray fluorescence analyzer of the present invention, it is possible to switch signal processing methods according to X-ray energy. In this way, regions for which energy resolution is significant are separated from regions where energy resolution is not so significant and it is possible to reduce the signal processing time for regions where resolution is not significant. This makes it possible to perform efficient measurement.

What is claimed is:

1. An energy dispersive X-ray analyzer, comprising:
   an energy dispersive X-ray detector for detecting X-rays and outputting a signal containing energy information of the detected X-rays,
   an X-ray counting section for analyzing the signal from the energy dispersive X-ray detector and generating a frequency distribution for each energy, the X-ray counting section having selection means for automatically selecting a particular signal processing method corresponding to the X-ray energy from a plurality of signal processing methods, and
   a data control section for performing data processing and user interface.

2. An energy dispersive X-ray analyzer, comprising:
   an energy dispersive X-ray detector for detecting X-rays and outputting a signal containing energy information of the detected X-rays,
   an X-ray counting section for analyzing the signal from the energy dispersive X-ray detector and generating a frequency distribution for each energy, the X-ray counting section having a selection section for automatically selecting a particular signal processing method corresponding to the X-ray energy from a plurality of signal processing methods, and
   a data control section for performing data processing and user interface.

* * * * *